(12) United States Patent
Tatar et al.

(10) Patent No.: US 9,816,937 B2
(45) Date of Patent: Nov. 14, 2017

(54) SENSOR FOR DETECTING WATER IN OIL

(71) Applicant: Aktiebolaget SKF, Göteborg (SE)

(72) Inventors: Florin Tatar, Delft (NL); Jozef Maria Storken, Nieuwegein (NL)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/309,876

(22) PCT Filed: Apr. 20, 2015

(86) PCT No.: PCT/EP2015/058487
§ 371 (c)(1),
(2) Date: Nov. 9, 2016

(87) PCT Pub. No.: WO2015/180891
PCT Pub. Date: Dec. 3, 2015

(65) Prior Publication Data
US 2017/0176340 A1 Jun. 22, 2017

(30) Foreign Application Priority Data

May 26, 2014 (GB) .................................. 1409303.3

(51) Int. Cl.
*G01N 21/85* (2006.01)
*G01N 33/28* (2006.01)

(52) U.S. Cl.
CPC ..... *G01N 21/8507* (2013.01); *G01N 33/2847* (2013.01)

(58) Field of Classification Search
CPC .................... G01N 21/8507; G01N 33/2847
See application file for complete search history.

(56) References Cited

U.S. PATENT DOCUMENTS 7,339,657 B2 * 3/2008 Coates ................... G01N 21/31
                                                                250/339.12
7,768,646 B1    8/2010 Mentzer et al.
(Continued)

FOREIGN PATENT DOCUMENTS

EP        2009438 A1     12/2008
WO    2007042501 A1      4/2007
(Continued)

*Primary Examiner* — Mark R Gaworecki
(74) *Attorney, Agent, or Firm* — Bryan Peckjian; SKF USA Inc. Patent Dept.

(57) ABSTRACT

A system for detecting the presence of water in oil, provides a detection head including a gap in which oil to be monitored may be received; at least a first optical fiber having a first end, optically coupled to transmit light across the gap; a micro electro-opto-mechanical (MEOM) device, the MEOM device comprising a photo-emitter and a photo-detector integrated onto a silicon based substrate, the photo-emitter being optically coupled to transmit light into a second end of the first optical fiber and the photo-detector being arranged to receive transmitted light that has been transmitted across the gap; and an electronic interface to the MEOM device for communicating therewith. A processor may be provided to analyze and compare the respective light signals to determine an amount of water present in the oil. By observing variations in absorption, the presence of water can be identified.

14 Claims, 4 Drawing Sheets

(56) References Cited

U.S. PATENT DOCUMENTS

| | | |
|---|---|---|
| 2004/0201835 A1 | 10/2004 | Coates et al. |
| 2009/0216464 A1 | 8/2009 | Kong et al. |
| 2009/0310138 A1 | 12/2009 | Vanhanen et al. |
| 2011/0249257 A1 | 10/2011 | Wildschuetz et al. |
| 2012/0112072 A1 | 5/2012 | Jones et al. |
| 2013/0016336 A1 | 1/2013 | Xie |

FOREIGN PATENT DOCUMENTS

| | | | | |
|---|---|---|---|---|
| WO | 2014039315 A2 | 1/2014 | | |
| WO | 2014090309 A1 | 6/2014 | | |
| WO | WO 2014090315 A1 * | 6/2014 | ......... | G01N 33/2847 |
| WO | 2015090359 A1 | 6/2015 | | |

\* cited by examiner

SENSOR FOR DETECTING WATER IN OIL

CROSS REFERENCE TO RELATED APPLICATIONS

This is a United States National Stage Application claiming the benefit of International Application Number PCT/EP2015/058487 filed on Apr. 20, 2015, which claims the benefit of British Patent Application 1409303.3 filed on May 26, 2014, both of which are incorporated herein by reference in their entireties.

FIELD OF THE INVENTION

The present invention relates to oil condition monitoring and in particular, to a sensor for detecting the presence of water in oil or like substances. The invention relates particularly to a micro electro-opto-mechanical device for such detection and to a method of monitoring the presence of water in oil allowing low-cost implementation.

BACKGROUND OF THE INVENTION

Optical sensors have been used for oil condition monitoring for determining the presence of debris or otherwise monitor deterioration of a lubricant. Such devices may operate by shining light through a small gap and analyzing the transmitted light with a suitable optical sensor. Alternative sensors may make use of scattering of light and may operate over different frequencies including outside of the visible range. Oil condition monitoring may be significant in providing feedback in advance of likely failure of a lubricant system. Action may be taken to perform maintenance or otherwise renew the lubricant.

Water in oil is of considerable concern to many mechanical systems. Minimal amounts of water may be absorbed by the oil during use, either from the atmosphere or by direct ingress of water into the system. As long as this water is in the absorbed state and the oil is unsaturated, the concern is minimal. Nevertheless, as the concentration of water approaches the saturation level, emulsified and free water may occur, which can be highly detrimental, especially if exposure is prolonged. In bearings, the incompressibility of water relative to the oil can result in disruption of the oil film leading to excessive wear. Just one percent water in oil can reduce the life expectancy of a bearing by as much as 90 percent. For ball or rolling element bearings, the localized pressure generated can cause spontaneous vaporization of the water, leading to erosive wear such as micropitting. The saturation level of water in oil may vary widely according to temperature and the type of oil and can range from 10 ppm to even 10000 ppm. Existing sensors capable of measuring the presence of water (free and dissolved) include capacitive sensors and Karl Fischer titration sensors. Both of these methods require considerable time for the sensor to reach equilibrium and are not ideal for rapidly changing conditions. Spectral analysis using Fourier Transform Infrared Spectroscopy (FTIR) has been used but is a relatively complex and costly procedure requiring calibration of the sensor relative to the spectrum produced with fresh oil. Spectral analyzers are also relatively costly, bulky and sensitive devices for installation in many environments where mechanical systems are located.

It would thus be desirable to provide for a low-cost and simple sensor arrangement that could reliably identify the presence of water in oil in real time.

BRIEF SUMMARY OF THE INVENTION

According to the invention there is provided a system for detecting the presence of water in oil, comprising: a detection head comprising a gap in which oil to be monitored may be received; at least a first optical fiber having a first end, optically coupled to transmit light across the gap; a micro electro-opto-mechanical (MEOM) device, the MEOM device comprising a photo-emitter and a photo-detector integrated onto a silicon based substrate, the photo-emitter being optically coupled to transmit light into a second end of the first optical fiber and the photo-detector being arranged to receive transmitted light that has been transmitted across the gap; and an electronic interface to the MEOM device for communicating therewith. In this context a MEOM device is intended to include any miniature electro-opto-mechanical device that is integrated onto a single semiconductor chip. The proposed MEOM device can be inexpensively produced by mass production techniques, making the system relatively inexpensive. Such systems may be permanently integrated into mechanical systems for conditioning monitoring purposes.

Various implementations of the system may be foreseen. In particular, the detection head may be either transmissive or reflective. In the former case, a second optical fiber may be provided, having a first end optically coupled to receive transmitted light, transmitted across the gap from the first end of the first optical fiber and having a second end optically coupled to transmit light to the photo-detector. In the alternative reflective implementation, the gap may provide a reflective surface opposite to the first end of the first optical fiber and arranged to reflect transmitted light back into the first end of the first optical fiber. The second end of the first optical fiber is then also optically coupled to the photo-detector. the light source and the interferometer may be coupled via an optical switch. The photo-emitter and photo-detector may be coupled to the second end of the first optical fiber by an optical switch, which may be in the form of a semi-reflective mirror or prism. Other similar beam splitters may also be used. These transmissive and reflective arrangements have been further described in related applications WO2014/090315 and PCT/EP2013/076791, the contents of which are hereby incorporated by reference in their entirety.

The photo-emitter may be any suitable light source. In one preferred form, it provides a light emitting diode (LED), in particular a broadband LED. It may also be an incandescent light source. The photo-emitter is preferably operable to transmit light over a broad spectrum in the IR region. The IR region in the range from 850 nm to 1750 nm is particularly favorable. Near infra-red light shows good absorption properties for water while being only slightly affected by other contaminants in the oil.

The light may be detected over a broad spectrum. Most preferably however, the photo-detector provides a spectrally selective detector operable to detect light over a narrow band of 100 nm or less, preferably in the regions around 1250 nm and/or 1400 nm. The light is thus analyzed in regions of the spectrum where water absorption peaks are present. For most oils, such absorption peaks may be identified at around 1250 nm and around 1400 nm and analysis in one or both of these specific regions is preferred.

The MEOM device preferably provides appropriate micro-machined light guides for guiding the transmitted light to the photo-detector. The light preferably enters the MEOM device through a window, such as a sapphire window, and may be further focused by appropriate lenses towards the photo-detector. The construction of the MEOM device may be otherwise conventional. The MEOM device may further provide a diffraction grating, arranged within the light guide to selectively direct chosen wavelengths of the transmitted light onto the photo-detector. The diffraction grating is preferably micro-machined together with the MEOM device as an integrated solution, whereby the diffraction grating and photo-detector act as a miniature spectro-analyser. Devices of this type are available such as the NIR 1.7 Microspectrometer from Insion™.

The system preferably further comprising a processor, operatively connectable to the electronic interface for driving and interrogating the MEMS device. The processor may be a stand-alone device dedicated to the MEOM device or may be part of a larger system such as a computer. Preferably, the processor is arranged to monitor a light signal representing light received at the photo-detector and to determine an amount of fluctuation of the light signal with time. The processor may further be arranged to compare the amount of fluctuation with a predetermined value representing a saturation level of the oil. The principle by which this saturation level may be determined is extensively described in related application PCT/EP2012/075437. Accordingly, it has been observed that a significant change in signal characteristic of the transmitted light is to be observed at the point at which free water appears in the oil. Below the saturation level, the transmitted light signal as received by the photo-detector is relatively stable and only steadily decreases in intensity with increasing absorbed water content. As the amount of water approaches saturation, the light signal becomes highly unstable and may appear noisy. Without wishing to be bound by theory, it is believed that bubbles of free water are formed within the oil in a manner similar to cavitation or boiling of a liquid. As these bubbles pass through the gap, they disturb the signal, effectively leading to greater absorption of the light and a lower light signal. A significant advantage of the above effect is that the system can be easily calibrated in-situ to the saturation level, without requiring knowledge of either the oil or system characteristics. Additionally, the system can provide real-time results with negligible delay in identifying the presence of free water in the oil.

The system as described above may be implemented in any situation where monitoring of oil condition is required. Most preferably, the detection head is located in an oil supply line of a mechanical system such as a gearbox, engine, bearing or the like.

The invention also relates to a method for detecting the presence of water in oil using a system as described above or hereinafter. The method may provide passing light through the oil from the photo-emitter to the photo-detector; monitoring the light signal received at the photo-detector; and analyzing and comparing the light signal to determine an amount of water present in the oil. Analysis of the light signal to determine an amount of fluctuation of the signal may provide monitoring the amount of fluctuation of the light signals to identify a step change representing saturation of the oil and generating a saturation signal indicative of saturation when the light signal indicates fluctuation of more than a predetermined value.

In one embodiment, determining an amount of fluctuation may provide measuring a peak to peak variation of the light signal within a sampling period. The sampling period may be chosen depending on various factors, including the sampling rate at which measurements of the light signal are taken and also based on physical factors such as the flow rate of the oil being monitored, the nature of the oil and other physical factors. In general, with the onset of free water the signal fluctuation may increase ten-fold or more and a predetermined value of 5 may be sufficient to provide reliable indication while avoiding false alarms. In other circumstances, a predetermined value of 2 may provide more sensitive response and predetermined values of below 2 may be applicable, in particular where signal smoothing has previously been applied. It will be understood that the sampling period will include at least two samples, preferably at least four samples and more preferably at least 10 samples. The sampling period may be between 1 second and 10 seconds, preferably between 2 seconds and 5 seconds. A sample rate of between 1 Hz and 10 Hz may be used, preferably around 2 Hz, again depending on the flow rate. In general, for a higher flow rate of the oil through the gap, a higher sample rate may be required for the same sensitivity.

According to one method of analysis, saturation may be identified when a ratio of the light signal fluctuation in a second sampling period to the light signal fluctuation in a first sampling period exceeds a predetermined value. The predetermined value may be determined according to the nature of the oil and other physical factors. In general, with the onset of free water the signal fluctuation may increase ten-fold or more and a predetermined value of 5 may be sufficient to provide reliable indication while avoiding false alarms. In other circumstances, a predetermined value of 2 may provide more sensitive response and predetermined values of below 2 may be applicable, in particular where signal smoothing has previously been applied.

According to a further aspect of the invention, the method may further provide determining the time that the oil remains above its saturation level. Once free water is detected in the oil, a timer may register the time elapsed until the danger of free water has receded. This point may be determined by evaluating a number of successive sampling periods and determining that water is absent once absence of saturation signal has been determined for all of these periods. Alternatively, once an absolute value of the light signal corresponding to the saturation level has been determined, the absence of free water may be indicated once the absolute value of one or more of the light signals returns to a value distant from the saturation level.

According to an alternative method, the exposure of the system to free water may be determined by integrating the saturation signal with respect to time. Based on a flow rate of the oil through the sensor, integration of the signal may allow an approximate determination of the total amount of free water in the system. This may be used to provide further alarms and initiate appropriate actions in the event that a given exposure is exceeded.

A significant advantage of the present invention is that the sensors need not be pre-calibrated and may be calibrated in-situ based on recognition of the saturation level. In the event that greater accuracy is required in the region of absorbed water, the method may provide calibrating the sensors for a sample of oil having a water content below the saturation level and subsequently determining a linear relation between the light signal and the water content when saturation of the oil is detected. Such a simple calibration may be achieved in a laboratory by calibrating the sensors against a Karl Fischer titration result. Alternatively, the sensors may be calibrated in the field by taking an oil sample for off-line analysis. Once calibrated, the sensors may be accurately used to also identify emulsified water in oil before the advent of free water.

The processor may be any appropriate processing device such as a computer or dedicated microprocessor. In addition to other control tasks, the processor is preferably arranged to determine when the fluctuation of the light signal exceeds the preset value. In particular the processor may carry out signal analysis, sampling and filtering as described above.

BRIEF DESCRIPTION OF THE SEVERAL VIEWS OF THE DRAWING

The features and advantages of the invention will be appreciated upon reference to the following drawings of a number of exemplary embodiments, in which.

DETAILED DESCRIPTION OF THE INVENTION

Figure 1:
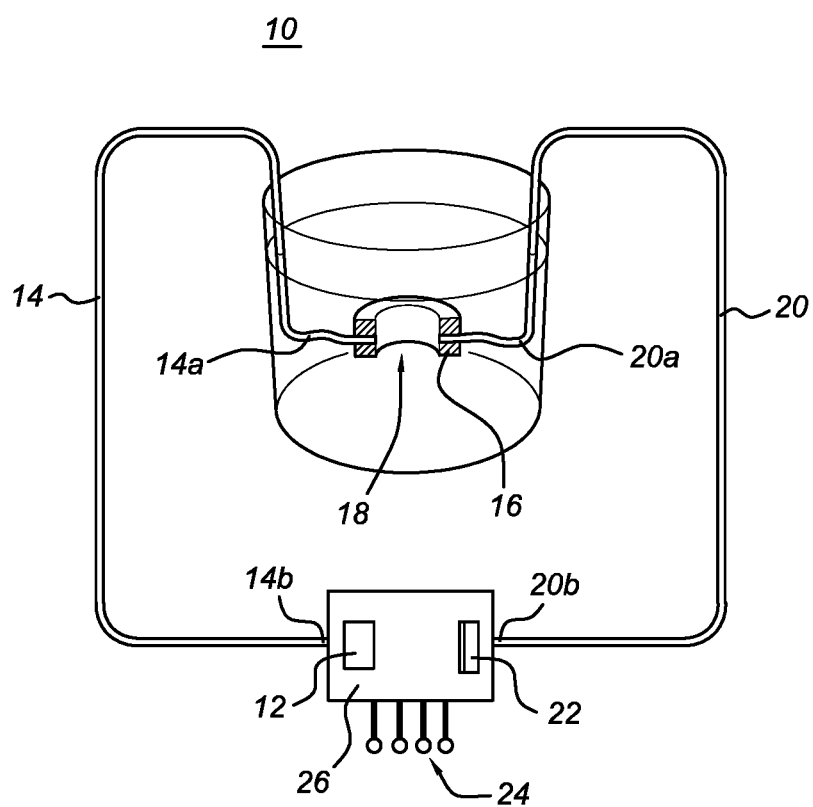
FIG. 1 shows a schematic view of a system according to the invention for determining the absorption spectrum of an oil sample.

FIG. 1 shows a schematic view of a system 10 for determining the absorption spectrum of an oil sample. The system provides a photo-emitter 12, a first optical fiber 14, a detector head 16 comprising a gap 18, a second optical fiber 20, a photo-detector 22 and an electronic interface 24. The photo-emitter 12, the photo-detector 22 and the electronic interface 24 are integrated together onto a Micro Electro-Opto-Mechanical (MEOM) device 26. The first optical fiber 14 has a first end 14a coupled to the detector head 16 and directed to transmit light across the gap 18 towards a first end 20a of the second optical fiber 20. A second end 14b of the first optical fiber 14 is coupled to the MEOM device 26 and optically coupled to receive light from the photo-emitter. A second end 20b of the second optical fiber 20 is also coupled to the MEOM device 26 and optically coupled to transmit light to the photo-detector 22.

Figure 2:
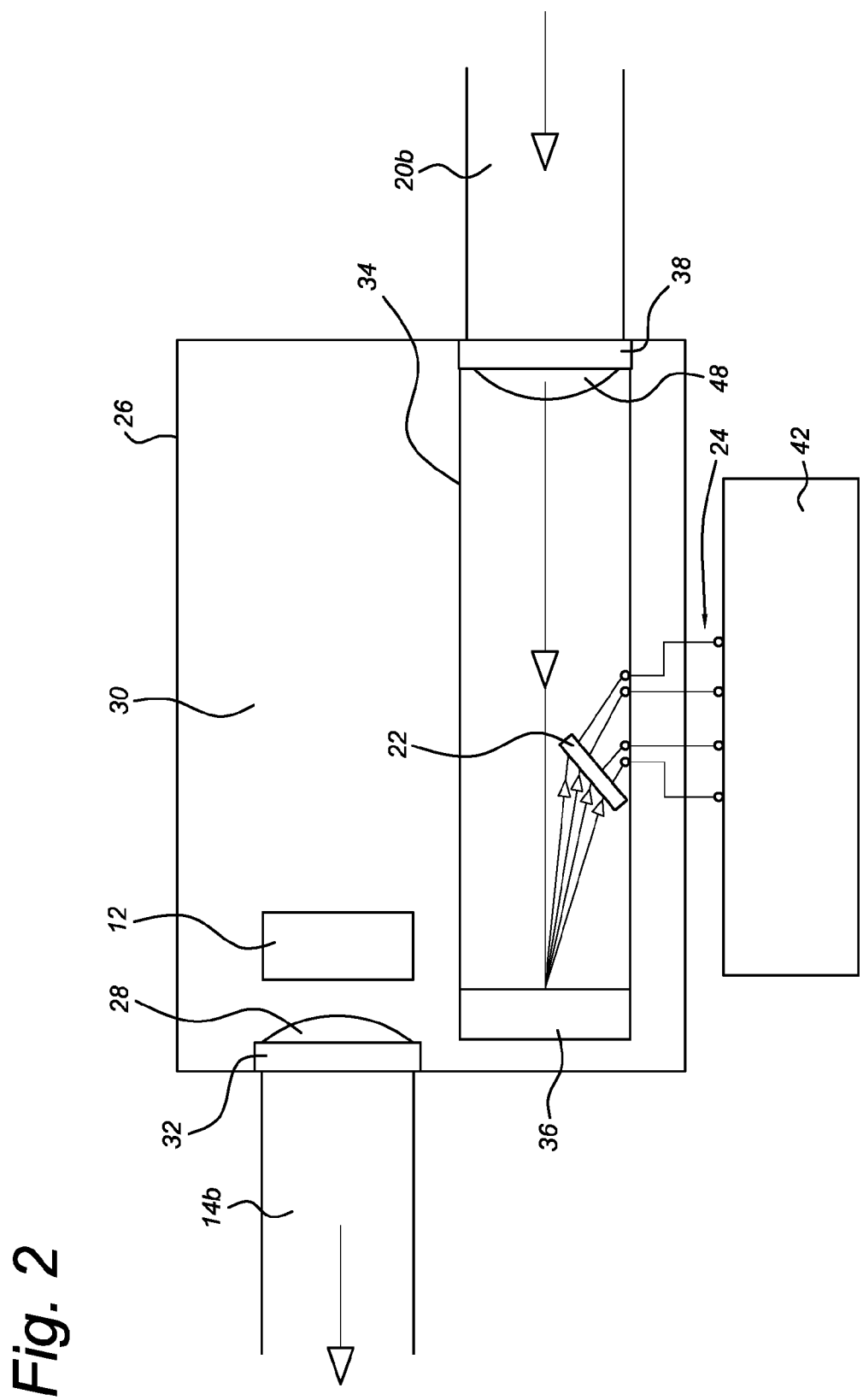
FIG. 2 shows a schematic view of part of the system of FIG. 1 in greater detail.

FIG. 2 is a detailed view of the MEOM device 26 of FIG. 1. The MEOM device 26 provides a silicon substrate 30 onto which the various components have been fabricated using appropriate micro-electronic fabrication procedures. The photo-emitter 12 is fabricated on a region of the substrate 30 adjacent to the second end 14b of the first fiber 14 and is coupled into it by a first silicon lens 28 and first sapphire window 32. A light guide 34 is formed across the substrate 30 from the second end 20b of the second fiber 20 to a diffraction grating 36 located at an opposite side of the substrate 30. The second end 20b of the second fiber 20 is coupled into the light guide 34 through a second sapphire window 38 and second silicon lens 40. To one side of the light guide 34 is located the photo-detector 22, interconnected to the electronic interface 24. Also shown is a processor 42 that is connected to receive signals from the MEOM device 26 via the electronic interface 24. It will be understood that the processor 42 may be a dedicated processor or a remote processor e.g. forming part of a computer and that the signals from the MEOM device may be transmitted by any appropriate manner.

Figure 3:
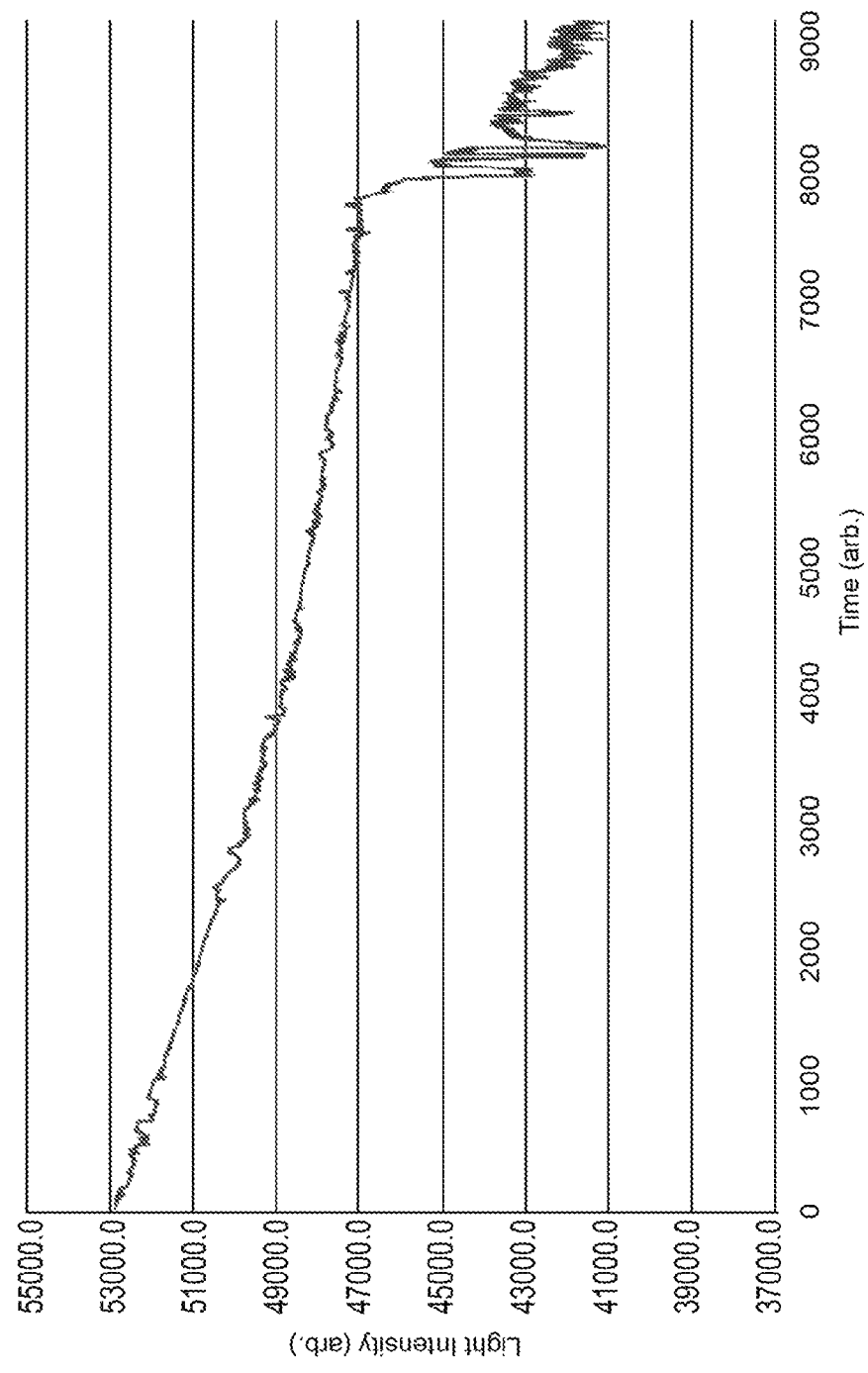
FIG. 3 shows light intensity measurements for increasing water content measured in the system of FIG. 1 for the wavelength of 1108 nm.

FIG. 3 shows a representative trace of the signal that may be expected using the system of FIGS. 1 and 2. Based on testing in a test setup the transmitted light received through a gap of 0.5 mm for an oil sample is shown as recorded over a number of hours, during which the concentration of water in the oil was steadily increased until the saturation level was reached (100% saturated). After this the water concentration was further increased to about 0.4% water. The light intensity measurements for the test are shown in FIG. 3 for the wavelength of 1108 nm. The result shows a strong and stable response to the ever increasing levels of water content. As the sample reaches saturation, the sensor records significant fluctuation in the signal. The sampling rate was 2 Hz. The skilled person will recognize that digital filtering such as a moving point average could be used to further smooth the signal.

Figure 4:
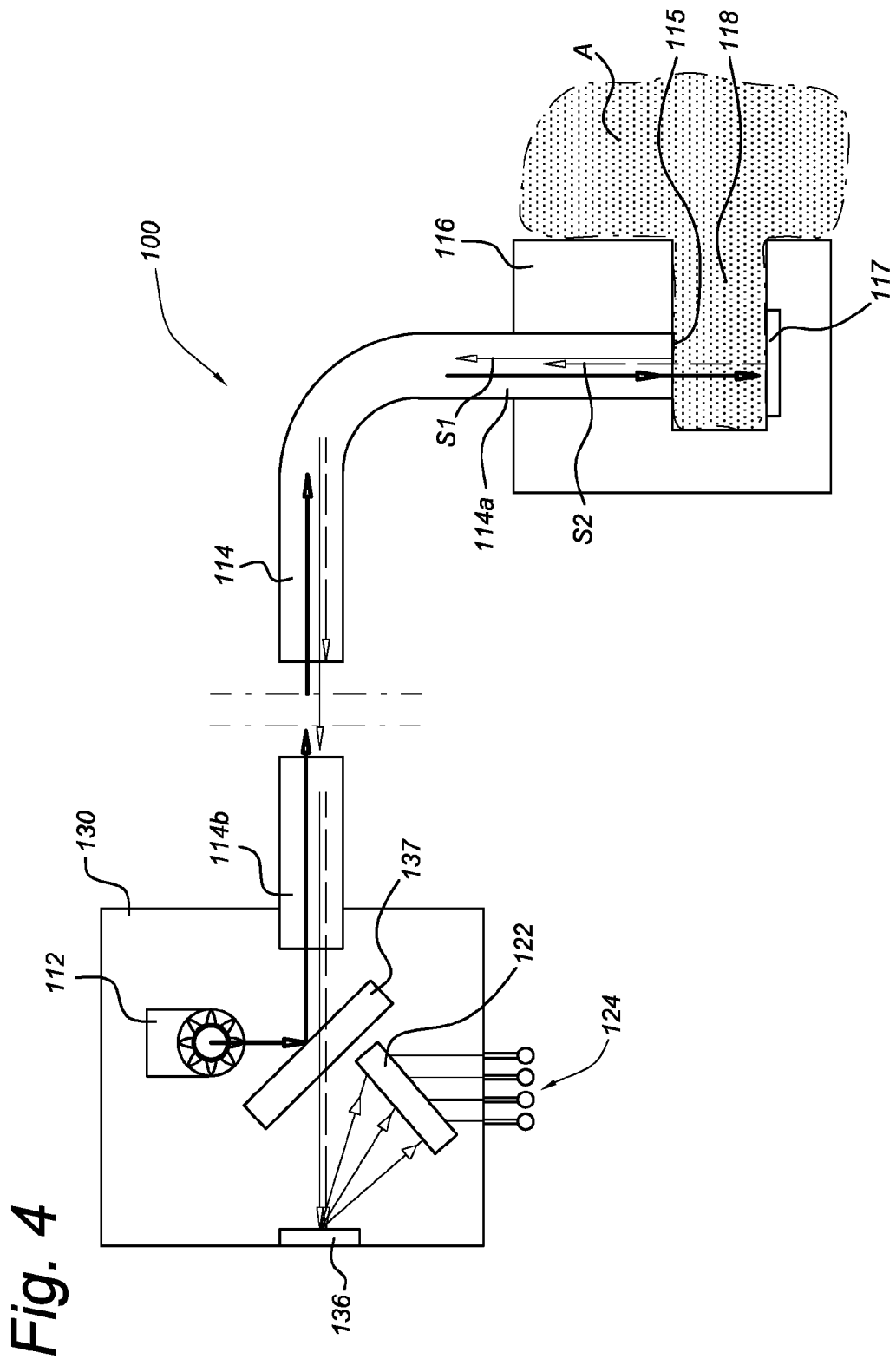
FIG. 4 shows a schematic view of an alternative system according to the present invention.

FIG. 4 shows a schematic view of a system 100 according to a second embodiment of the invention. In this embodiment, a single optical fiber 114 is used, coupled at its first end 114a to a detector head 116, having a gap 118. In this case, a surface of the detector head 116, facing the first end 114a of the optical fiber 114 is formed as a mirror 117, whereby light emitted from the optical fiber 114 is reflected back into the first end 114a thereof. The first end 114a of the optical fiber is also provided with a semi-reflective surface 115. The second end 114b of the optical fiber 114 is coupled to a MEOM device 126 comprising a photo-emitter 112, a photo-detector 122, an electronic interface 124 and a diffraction grating 136, integrated onto a substrate 130. Additionally, there is provided a semi-reflective mirror 137, which acts as an optical switch between the photo-emitter 112 and the diffraction grating 136 as described further in detail below.

In use, the detector head 116 is located within a mechanical system (not shown) such that oil A is received in the gap 118. Light from the photo-emitter 112 is coupled into the optical fiber 114 and guided through the optical fiber 114 to exit from the first end 114a. A portion of the light is reflected internally by the semi-reflective surface of the end face 115 and returns through the optical fiber as first light signal S1. The remainder of the light passes into and through the oil A in the gap 118 and impinges on the mirror 117, which reflects it back across the gap 118 and into the first end 114a of the optical fiber 114 as second light signal S2.

The first and second light signals S1, S2 are transmitted through the optical fiber 114 and the semi-reflective mirror 137 to the diffraction grating 136. The diffraction grating 136 is selectively deflects the different wavelengths onto the photo-detector 122 which can thus determine the frequency at which the signals S1, S2 constructively interfere. In general, once determined, this frequency will remain relatively stable for a given configuration and can be identified as a maximum in the combined signal S1+S2.

The first light signal S1 may be used as a reference signal. The second light signal S2 is added to the first light signal S1 to ensure interference. Any amplitude changes caused by the fiber 114 bending will influence both signals S1 and S2 in a fixed proportional way. In this way amplitude changes caused by the fiber 114 bending becomes a known factor. The actual amplitude change that represents an oil in water saturation level can be calculated by removing the known factor. The measurement system is therefore not restricted to any fixed geometry and is more robust in use.

Thus, the invention has been described by reference to the embodiment discussed above. It will be recognized that this embodiment is susceptible to various modifications and alternative forms well known to those of skill in the art without departing from the spirit and scope of the invention. In particular, it will be understood that many different algorithms and signal analysis procedures may be carried out to determine the oil condition based on the sensor outputs. Accordingly, although specific embodiments have been described, these are examples only and are not limiting upon the scope of the invention.

The invention claimed is:

1. A system for detecting a saturation level of water in oil, comprising:
    a detection head comprising a gap in which oil to be monitored may be received;
    at least a first optical fibre having a first end, optically coupled to transmit light across the gap;
    a micro electro-opto-mechanical (MEOM) device, the MEOM device comprising a photo-emitter and a photo-detector integrated onto a silicon based substrate, the photo-emitter being optically coupled to transmit light into a second end of the first optical fibre and the photo-detector being arranged to receive transmitted light that has been transmitted across the gap; and
    an electronic interface to the MEOM device for communicating therewith; wherein
    the photo-detector comprises a spectrally selective detector operable to detect light over a narrow band of 100 nm or less, in the regions around 1250 nm or 1400 nm.

2. The system of claim 1, further comprising a second optical fibre, having a first end optically coupled to receive transmitted light, transmitted across the gap from the first end of the first optical fibre and having a second end optically coupled to transmit light to the photo-detector.

3. The system of claim 1, wherein the gap comprises a reflective surface opposite to the first end of the first optical fibre and arranged to reflect transmitted light back into the first end of the first optical fibre and the second end of the first optical fibre is also optically coupled to the photo-detector.

4. The system according to claim 1, wherein the photo-emitter comprises a light emitting diode.

5. The system according to claim 1, wherein the photo-emitter is operable to transmit light over a broad spectrum in the IR region.

6. The system according to claim 1, wherein the MEOM device further comprises a micro-machined light guide extending from a window, where the transmitted light enters the MEOM device, to the photo-detector.

7. The system according to claim 6, wherein the MEOM device further comprises a diffraction grating, arranged within the light guide to selectively direct chosen wavelengths of the transmitted light onto the photo-detector.

8. The system according to claim 1, further comprising a processor, operatively connectable to the electronic interface for driving and interrogating the MEOM device.

9. The system according to claim 8, wherein the processor is arranged to monitor a light signal representing light received at the photo-detector and to determine an amount of fluctuation of the light signal with time.

10. The system according to claim 9, wherein the processor is arranged to compare the amount of fluctuation with a predetermined value representing a saturation level of the oil.

11. The system according to claim 1, wherein the detection head is located in an oil supply line of a mechanical system.

12. A method for detecting presence saturation level of water in oil using the system according to any preceding claim, comprising passing light through the oil from the photo-emitter to the photo-detector; monitoring the light signal received at the photo-detector; and analysing and comparing the light signal to determine an amount of water present in the oil.

13. The method of claim 12, further comprising analysing the light signal to determine an amount of fluctuation of the signal; monitoring the amount of fluctuation of the light signals to identify a step change representing saturation of the oil and generating a saturation signal indicative of saturation when the light signal indicates fluctuation of more than a pre-set value.

14. The method of claim 13, wherein determining an amount of fluctuation comprises measuring a peak to peak variation of the light signal within a sampling period.

* * * * *